United States Patent [19]

Wong

[11] Patent Number: 4,665,148

[45] Date of Patent: May 12, 1987

[54] STABILIZED SILICONE GELS

[75] Inventor: Ching-Ping Wong, Lawrence Township, Mercer County, N.J.

[73] Assignee: AT&T Technologies, Inc., Berkeley Heights, N.J.

[21] Appl. No.: 805,599

[22] Filed: Dec. 10, 1985

Related U.S. Application Data

[63] Continuation of Ser. No. 677,681, Dec. 3, 1984, abandoned.

[51] Int. Cl.⁴ .............................................. C08G 77/06
[52] U.S. Cl. ....................................... 528/15; 528/31; 528/32; 525/478
[58] Field of Search ............................ 528/15, 31, 32; 525/478

[56] References Cited

U.S. PATENT DOCUMENTS

| | | | |
|---|---|---|---|
| 4,008,346 | 2/1977 | Moeller | 556/450 |
| 4,011,247 | 3/1977 | Sato et al. | 556/451 |
| 4,043,977 | 8/1977 | de Montigny et al. | 528/21 |
| 4,066,594 | 1/1978 | Moeller | 556/453 |
| 4,336,364 | 6/1982 | Maxson | 528/29 |

Primary Examiner—Melvyn I. Marquis
Attorney, Agent, or Firm—J. F. Spivak

[57] ABSTRACT

A method for preventing unwanted continued polymerization with aging of a polymer, e.g., a silicone gel, which was catalytically cured comprises treating the cured polymer with a catalytic deactivating agent or stabilization of cured resin.

4 Claims, 4 Drawing Figures

STABILIZED SILICONE GELS

This is a continuation of application Ser. No. 677,681, filed 12/3/84, now abandoned.

TECHNICAL FIELD

This invention relates to silicone resin formulations and articles made therefrom and particularly to silicone gels which have been formed by curing of silicones in the presence of a metal catalyst.

BACKGROUND OF THE INVENTION

Silicone polymers are well known in the polymer art. They enjoy a wide variety of uses such as encapsulants and coatings for the electronics industry, sealants and greases, medical implants and in the media for certain types of touch sensitive displays. In many instances, the silicone polymer is formed by polymerization of a silicone or mixture of silicones in the presence of a pt catalyst. Further, in many instances it is desired to stop the polymerization process in order to achieve a silicone polymer which has a certain desired consistency such as a gel consistency. This is true, for example, for both silicone implants used in the medical industry for such things as breast implants, as well as the silicone formulation employed in touch sensitive screens for electro-optical display devices. A problem that has been found to exist with such silicones is that, with time, the curing process continues resulting in an undesirable hardening or thickening so as to change the consistency of the silicone from the desired consistency to one that is undesirable. I have now discovered a means for substantially terminating the polymerization process after the desired consistency is reached so as to prevent the hardening that occurs with age in silicone formulations cured by means of a pt catalyst.

SUMMARY OF THE INVENTION

This invention includes the method of producing a silicone polymer of a desired consistency as well as the resulting polymer and articles of manufacture made therefrom. The method involves curing a silicone formulation in the presence of a pt catalyst so as to form a desired consistency and then treating the polymerized silicone with ammonia so as to effectively deactivate the catalyst without degrading the polymer. The resulting polymer of the desired consistency therefore contains a catalyst which has been deactivated such that further polymerization is substantially reduced. Such polymerized material can then be employed in the manufacture of articles such as breast implants and touch sensitive screens as examples.

DETAILED DESCRIPTION

Figure 1:
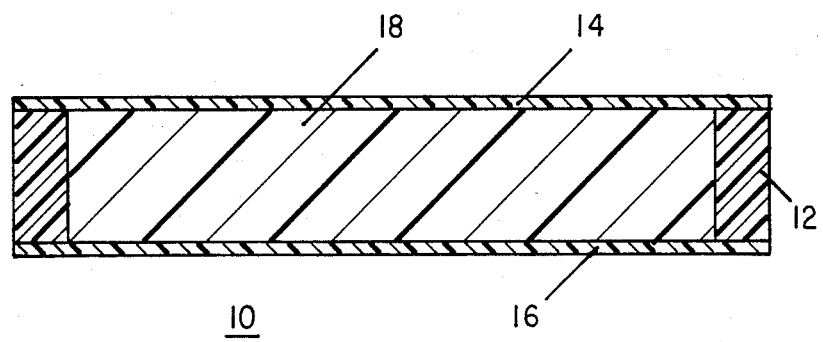
FIG. 1 is a side elevational cross-sectional view of a touch sensitive screen.

While this invention is described in terms of forming silicone gels and articles incorporating such gels from the polymerization of mixtures of silicone materials in the presence of a platinum catalyst, it should be understood that the concept herein, involving the deactivation of a catalyst or cured resin in order to insure the cessation of further polymerization or crosslinking subsequent to reaching the desired consistency of material, is equally applicable to any silicone formulation which is polymerized or crosslinked by means of any catalyst capable of being deactivated in a similar fashion.

One method of forming silicone gels, for example, is the reaction of two silicone polymers having an addition reaction curing system in the presence of a platinum catalyst. For example, upon mixing a silicone hydride with a silicone polymer containing a vinyl group either at the end of a chain or along the siloxane chain (pendant groups), in the presence of a small amount of a platinum catalyst, e.g., in the order of about 1–10, ppm, an addition reaction occurs. When the vinyl groups are at the end of a chain, chain extension results while if the vinyl groups are along the chain a higher density crosslinking reaction results. Examples of such reactions are given below:

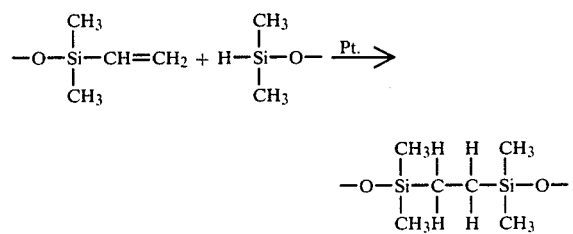

End group reaction (lengthen molecule)

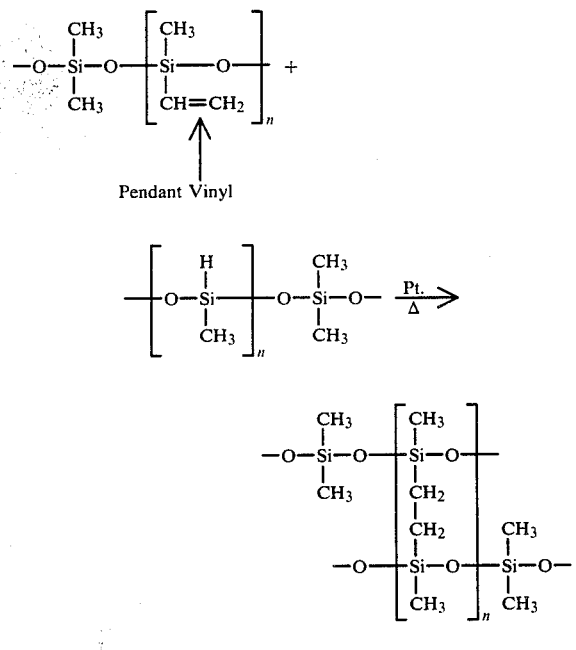

Higher Cross-link density reaction

Another possible reaction mechanism involving the cured silicone gel which could lead to continued crosslinking is shown below.

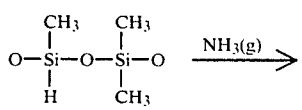

cured gel
(Reactive)

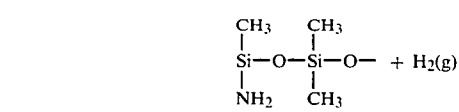

amino siloxane
(Still Reactive)

or

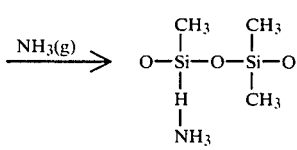

Theoretically, there are no volatile byproducts produced during this cure. However, hydrogen gases are always obtained during the cure due to other side reactions. If the number of Si-H groups of a silicone hydride exceeds the number of vinyl groups in the vinyl containing silicone compound such that the ratio of Si-H/Si-vinyl is greater than one, a gel results. If on the other hand, that ratio is less than one, i.e., the number of Si-vinyl groups exceeds the number of Si-H groups, then an elastomer is produced. Useful platinum catalysts are known in the industry. They are generally in the form of platinum salts. One commerically employed Pt catalyst used in silicone formulations is prepared by reducing $H_2PtCl_6$ with $NaHCO_3$ and reacting the resultant divalent platinum salt with a silane or low molecular weight siloxane, e.g., divinyl tetramethoxy silane or low molecular weight divinyl polydimethyl siloxane. The reason for the reaction with the silane or siloxane is to increase its solubility in the formulation.

An alternative method of preparing such silicones involves a condensation reaction curing system in which an alkoxy crosslinker reacts with a silanol group in the presence of a stannous soap as the catalyst.

Applications for these versatile materials are numerous and span various industries including the automative, aerospace, appliance, electrical and medical industries. Generally, lightly crosslinked addition reaction systems can be engineered to produce soft, clear vibration absorbing gels which may either be used in the electornics industry to pot delicate assemblies or as the primary component of a touch screen cathode ray tube which operates based upon the deflection of light upon pressure placed on the screen. Another use of such a gel is in the implantable breast prosthesis in the medical industry. Increased crosslinking leads to harder and tougher silicones which enjoy many other uses as is well known in the art.

A problem which exists in articles made from silicone gels is that, after time, there is often a tendency for the gel to undesirably harden and also to produce gas bubbles. I have discovered that this hardening is due primarily to the diffusion of water vapor into the gel and the reaction of this water vapor in the presence of the active catalyst, e.g., platinum, to form active siloxy or silanol groups which react either with each other or with unreacted hydrogen atoms contained on silicone hydride bonds so as to induce further crosslinking. These reactions result in the formation of hydrogen gas which is the cause of the bubbles. Typical reactions of the type suspected are shown below:

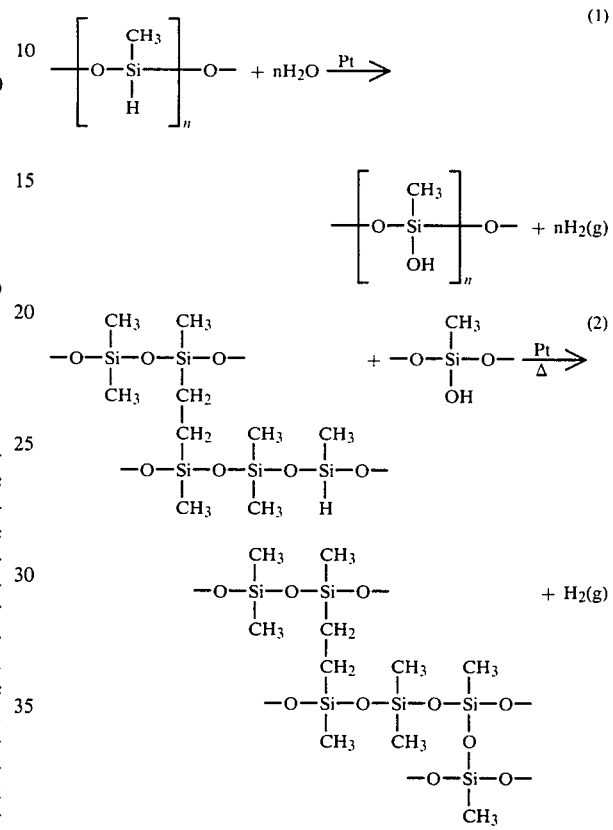

I have discovered that this aging reaction can be substantially eliminated by the deactivation of the catalyst or cured resin. Such deactivation can be accomplished, for example, by subjecting the gel or the article containing the gel to an atmosphere which diffuses into the gel and reacts with the catalyst or cured resin so as to deactivate it. It is believed that platinum (Pt) and other metal-containing catalysts function by way of an active electron-pair acceptor site on the metal atom or ion and, if the availability of that site to accept electrons is removed the catalytic activity can be eliminated. For example, the catalytic action of platinum can be poisoned or deactivated by reacting the platinum with an electron pair donor such as a nitrogen or other atom having a free electron pair, the nitrogen atom thereby bonding to the Pt atom removing the electron-pair acceptor site. Hence, by either exposing the gel containing article to an atmosphere having a vapor containing ammonia, or, by immersion in an ammonia solution for a sufficient time for the ammonia to diffuse through any polymeric cover or container so as to combine with and deactivate the platinum catalyst in the silicone polymer, one can limit or prevent the catalyst from catalyzing further crosslinking due to the diffusion of water vapor into the article.

In use, the silicone gels may be in the form of an article wherein the gel is encapsulated in a silicone elastomer or other polymeric material so as to be contained in a pouch or pouch-like member. The polymer forming the pouch like member is generally flexible yet rigid enough to retain a given shape when no pressure is applied. Such is the case with both the prosthesis and the touch sensitive screen previously mentioned.

One method of testing the efficiency of the treatment is to compare the height of the absorption peaks of the Si-H bond at ~2126cm$^{-1}$ by means of Fourier Transform Infrared spectroscopy of both treated and untreated samples which have been exposed to water vapor as compared to a freshly prepared silicone gel. If the catalyst has been deactivated such that the exposure to water does not cause further polymerization or crosslinking, the number of Si-H sites should remain constant. Consequently, a sample in which the catalyst has been deactivated and then treated in water vapor would show essentially the same height of the Si-H absorption peak as the freshly prepared sample while the untreated sample, after exposure to water vapor, would show a greatly reduced height of the Si-H absorption peak due to the reaction of the Si-H bond with the water vapor and ultimately with other Si-H or similar hydroxy groups resulting in further crosslinking.

Another measure of determining the effectiveness of the treatment is to test the force required to achieve a particular amount of deflection of the gel-containing article, e.g., the soft touch screen. Here, if a larger force is required after aging than before aging, one may conclude that the screen became harder due to further cross-linking. The results of such experiments are shown below.

Touch sensitive screens as shown in FIG. 1 useful in connnection with a CRT display as taught in U.S. Pat. No. 4,346,376 issued to J. B. Mallos or U.S. Pat. No. 3,673,327 illused to R. G. Johnson both of which are incorporated herein by reference were prepared utilizing a silicone gel prepared by curing a mixture of Dow Corning Silicones which comprises a silicone having a vinyl group in the chain and a silicone having Si-H groups. For example, one can employ Dow Corning's two pair heat curable system marketed as SCF3-9610. The screen 10 comprises a thick polyurethane frame 12, a thin polyurethane front cover layer 14 molded to one side of the frame 12, a thin polyurethane back cover layer 16 molded to the opposite side of the frame 12 such that the frame 12 and front and back and front cover layers 14 and 16 form a rigid, i.e., dimensionally stable yet flexible pouch which is filled with the silicone gel 18. A more detailed method of making such a screen can be found in U.S. patent application Ser. No. 715,280 filed on Mar. 25,1985 for Bogatin, et al. which is incorporated herein by reference.

The effect of aging on screens prepared in this manner was tested by measuring the force required to deflect the screen at a given distance and by observing the change in the ~2126cm$^{-1}$ peak with respect to a reference peak ~1923cm$^{-1}$ in the IR spectra.

Ten screens were exposed to ammonia vapors for 24 hours. These screens and ten unexposed control screens were placed in an oven a 70° C. to simulate accelerated aging. The hardness of the screens were measured at various times. The average force deflection measured for the unexposed controls and the ammonia exposed screens are given in Table I. It is apparent from the table that the ammonia treatment inhibited hardening i.e., further curing of the silicone polymer.

TABLE I

|  | Before Ammonia Treatment | After Ammonia Treatment | After 66 hrs. at 70 C. | After 122 hrs. at 70 C. |
| --- | --- | --- | --- | --- |
| Controls | 239.6 | — | 440.9 | 744.9 |
| Ammoniated | 218.4 | 258.1 | 294.9 | 312.0 |

Figure 2:
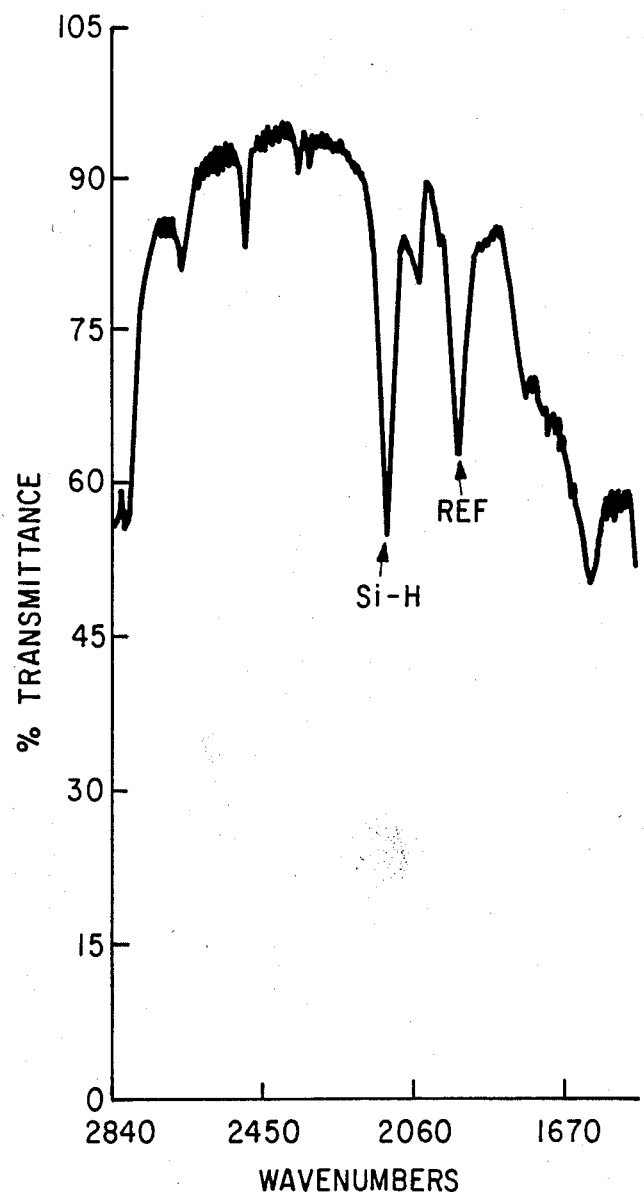
FIGS. 2–4 show the plot of percent transmission vs. wavenumber obtained from the FT-IR spectrophotometric analysis of a newly produced touch sensitive, silicone gel-filled screen (FIG. 2); a screen after exposure to moisture (FIG. 3); and a screen after treatment with NH$_3$ followed by exposure to moisture (FIG. 4).
Figure 3:
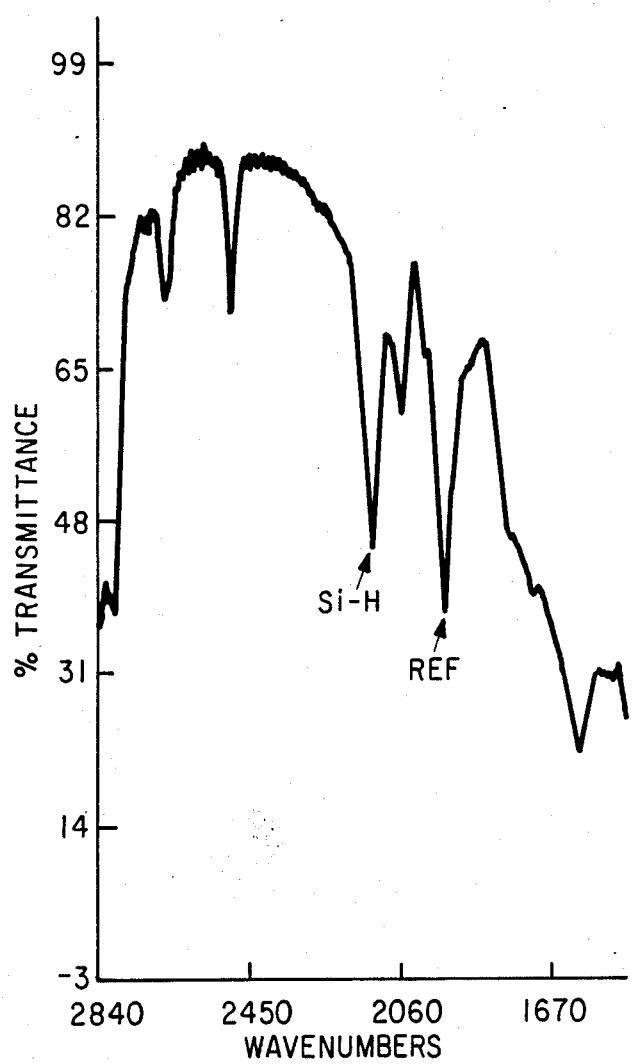
Figure 4:
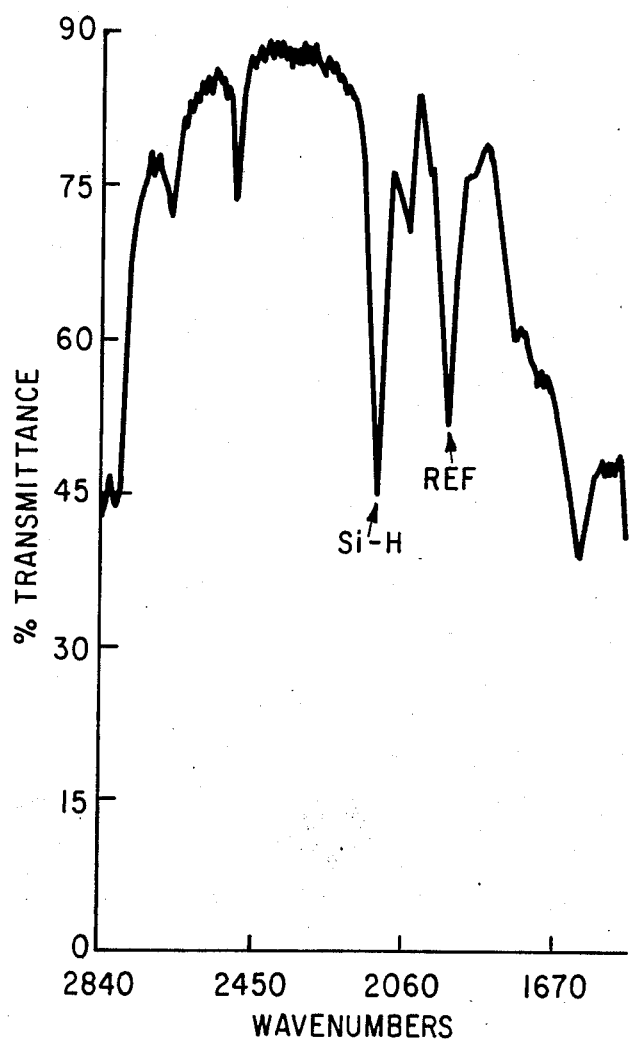

FIGS. 2-4, respectively, show a portion of the IR spectra of a control screen prior to any treatment (FIG. 2), a control screen which has been exposed to water (FIG. 3) and a screen which was treated with ammonia vapor for 24 hours prior to treatment with water (FIG. 4). As can be seen from the Figures, the relative absorption of the Si-H bond at ~2126cm$^{-1}$ and that of the reference peak, ~1923cm$^{-1}$, are the same for the control and the ammonia-treated sample indicating essentially no change in the concentration of Si-H bonds after exposure to water. However, the sample which was not pre-treated with ammonia shows a reversal with respect to the reference peak. This indicates further polymerization resulting in fewer remaining Si-H bonds.

It should be further understood that while this discovery is particularly suitable for maintaining the consistency of a silicone gel, it can also be utilized to prevent further curing of elastomers where there are unreacted Si-H bonds in the elastomer or wherever the combination of water vapor together with a catalyst can cause further polymerization or crosslinking of a polymer to an extent which is undesirable.

Further, while the above examples are limited to the deactivation of a platinum catalyst, as indicated previously, other catalysts such as tin soaps are sometimes used in the industry and similar techniques can be used to deactivate these catalysts as well. Hence, it is not intended that this invention be limited to any particularr catalyst but is directed to the concept of deactivating electron pair accepting catalyst so as to prevent reaction upon aging with water vapor in the presence of an active catalyst.

What is claimed is:

1. A method of limiting the continued curing of a silicone polymer which was polymerized in the presence of a platinum curing catalyst comprises the step of exposing the cured polymer to ammonia.

2. The method recited in claim 1 wherein the polymer is a silicone gel.

3. The method recited in claim 1 wherein the ammonia is in the form of vapors which diffuse into the polymer.

4. The method recited in claim 2 wherein the silicone gel is contained in a rigid polymeric container which is permeable to ammonia vapors.

* * * * *